(12) United States Patent
Shin et al.

(10) Patent No.: US 10,703,852 B2
(45) Date of Patent: Jul. 7, 2020

(54) ISOCYANATE COMPOSITION FOR OPTICAL LENSES AND PROCESS FOR PREPARING THE SAME

(71) Applicant: SKC CO., LTD., Suwon-si, Gyeonggi-do (KR)

(72) Inventors: Junghwan Shin, Suwon-si (KR); Hyuk Hee Han, Seongnam-si (KR); Jongmin Shim, Hwaseong-si (KR)

(73) Assignee: SKC CO., LTD., Suwon-si (KR)

( * ) Notice: Subject to any disclaimer, the term of this patent is extended or adjusted under 35 U.S.C. 154(b) by 73 days.

(21) Appl. No.: 15/980,265

(22) Filed: May 15, 2018

(65) Prior Publication Data
US 2018/0334531 A1 Nov. 22, 2018

(30) Foreign Application Priority Data
May 16, 2017 (KR) .................. 10-2017-0060524

(51) Int. Cl.
| | |
|---|---|
| *C08G 18/00* | (2006.01) |
| *C08G 61/04* | (2006.01) |
| *C08G 18/76* | (2006.01) |
| *C08G 18/38* | (2006.01) |
| *G02B 1/04* | (2006.01) |
| *C07C 263/10* | (2006.01) |

(52) U.S. Cl.
CPC ........ *C08G 18/7642* (2013.01); *C07C 263/10* (2013.01); *C08G 18/3876* (2013.01); *G02B 1/041* (2013.01)

(58) Field of Classification Search
CPC ............ C08G 18/7642; C08G 18/3876; G02B 1/041; C07C 263/10; C07C 265/14
USPC .................... 528/77, 76, 44; 520/1
See application file for complete search history.

(56) References Cited

U.S. PATENT DOCUMENTS

| | | | |
|---|---|---|---|
| 8,212,080 B2 | 7/2012 | Kumano et al. | |
| 2003/0013917 A1* | 1/2003 | Nakamura | C07C 209/48 564/373 |
| 2007/0010693 A1 | 1/2007 | Hugo et al. | |
| 2008/0009654 A1 | 1/2008 | Kumano et al. | |
| 2009/0020407 A1 | 1/2009 | Hugo et al. | |
| 2010/0168474 A1 | 7/2010 | Kumano et al. | |
| 2013/0296609 A1 | 11/2013 | Kumano et al. | |
| 2013/0303721 A1 | 11/2013 | Jang et al. | |
| 2014/0017429 A1* | 1/2014 | Kasazaki | C08L 23/0869 428/36.4 |
| 2017/0121449 A1 | 5/2017 | Maleika et al. | |

FOREIGN PATENT DOCUMENTS

| | | |
|---|---|---|
| EP | 1 279 661 A1 | 1/2003 |
| EP | 1 873 137 A1 | 1/2008 |
| JP | 2010-168374 * | 8/2010 |
| JP | 2010-168374 A | 8/2010 |
| KR | 2012-0076329 A | 7/2012 |

OTHER PUBLICATIONS

Kumano et al, JP 2010-168374 Machine Translation, Aug. 5, 2010 (Year: 2010).*
European Patent Office, Communication dated Sep. 17, 2018, issued in counterpart European Application No. 18170215.0.
Japanese Patent Office; Communication dated May 7, 2019 in counterpart Japanese Application No. 2018-093798.

* cited by examiner

*Primary Examiner* — Jessica Whiteley
(74) *Attorney, Agent, or Firm* — Sughrue Mion, PLLC

(57) ABSTRACT

An isocyanate composition is prepared from an amine composition, which comprises (a) 99% to less than 100% by weight of m-xylylenediamine; (b) greater than 0% to 0.5% by weight of p-xylylenediamine; and (c) greater than 0% to 0.5% by weight of at least one selected from the group consisting of benzylamine, 4-methylbenzylamine, and 4-cyanobenzylamine. Therefore, the isocyanate composition used in the preparation of a polythiourethane can be controlled to a specific composition in the synthesis thereof, which makes it possible to conveniently produce an optical lens with a high quality.

10 Claims, No Drawings

ISOCYANATE COMPOSITION FOR OPTICAL LENSES AND PROCESS FOR PREPARING THE SAME

TECHNICAL FIELD

Embodiments relate to an isocyanate composition for an optical lens and a process for preparing the same. More specifically, the embodiments relate to a process for preparing a xylylene isocyanate-based composition used as a raw material in the production of a polythiourethane-based lens having excellent optical properties and to a polymerizable composition, a polythiourethane, and an optical material obtained using the same.

BACKGROUND ART

Since plastics optical materials are lightweight, hardly breakable, and excellent in dyeability as compared with optical materials made of inorganic materials such as glass, plastic materials of various resins are widely used as optical materials for eyeglass lenses, camera lenses, and the like. Recently, there has been a demand for high performance of optical materials having such properties as a high transparency, a high refractive index, a low specific gravity, a high heat resistance, and a high impact resistance.

Polythiourethanes are widely used as an optical material by virtue of their excellent optical characteristics and excellent mechanical properties. Polythiourethanes may be prepared by reacting a thiol and an isocyanate. Lenses produced from polythiourethanes are widely used since they have a high refractive index, a lightweight, and a relatively high impact resistance.

Isocyanates used as a raw material of a polythiourethane are capable of producing polythiourethanes having different structures depending on the number and position of the functional groups in the isocyanates. Thus, the isocyanates have a significant impact on the physical properties of a product produced from the polythiourethane. Accordingly, a certain kind of isocyanate that can impart the desired properties to a final product is used.

Especially, since xylylene diisocyanate (XDI) has both characteristics of alicyclic isocyanates (e.g., resistance to yellowing, readily controllable reactivity, and the like) and those of aliphatic isocyanates (e.g., excellent mechanical properties, high refractive indices, and the like), it is possible to materialize excellent properties of an optical lens by taking advantage of the respective characteristics.

PRIOR ART DOCUMENT

Patent Document (Patent document 1) Korean Laid-open Patent Publication No. 2012-0076329 (Jul. 9, 2012)

DISCLOSURE OF INVENTION

Technical Problem

Xylylene diisocyanate is classified into o-XDI (ortho-XDI), m-XDI (meta-XDI), and p-XDI (para-XDI) according to the relative positions of the diisocyanate groups. m-XDI among these is the most widely used as a raw material for an optical lens since it is suitable for the physical properties of an optical lens and available in the market.

However, commercially available m-XDI, even purified, is likely to contain a small amount of heterogeneous components such as isomers or monoisocyanates. These heterogeneous components may cause side reactions at the time of producing a product, which deteriorates the physical properties of the product and is unfavorable for long-term storage, and which ultimately leads to a serious problem in the field of optical lenses in which a high level of transparency and optical characteristics are particularly required.

Therefore, it is necessary to remove the heterogeneous components contained in the raw materials of m-XDI prior to the production of a product. However, these heterogeneous components are generated even at the time of preparing xylylenediamine, which is a raw material of xylylene diisocyanate. Further, the chemical structure and chemical properties thereof are so similar that it has been difficult to identify them by a conventional method. In addition, efforts to remove all kinds of heterogeneous components are not only inefficient but also make the process complicated and incur high costs.

Accordingly, the present inventors have studied a number of heterogeneous components that may be incorporated into the raw materials of m-XDI and have endeavored to find the components that have a particularly significant impact on the properties required for optical lenses. As a result, it has been found that the properties of an optical lens can be effectively satisfied by controlling the content of certain specific heterogeneous components contained in the raw materials of m-XDI.

Therefore, the embodiments described hereinafter aim to provide a method of effectively satisfying the physical properties of an optical lens by identifying and controlling the kind and the content of the components, which significantly affect the physical properties required for optical lenses, among the heterogeneous components contained in the raw materials of m-XDI.

Especially, the embodiments aim to provide a method for easily adjusting the isocyanate component to a desired composition in the synthesis of the isocyanate by controlling an amine used as a raw material for the synthesis of the isocyanate, rather than directly controlling the isocyanate itself that is difficult to purify.

Solution to Problem

According to an embodiment, there is provided a process for preparing an isocyanate composition, which comprises preparing a first amine composition comprising m-xylylenediamine; reducing the content of at least one of p-xylylenediamine, benzylamine, 4-methylbenzylamine, and 4-cyanobenzylamine in the first amine composition to obtain a second amine composition; and synthesizing an isocyanate from the second amine composition.

According to an embodiment, there is provided an isocyanate composition, which comprises (a') 99% to less than 100% by weight of m-xylylene diisocyanate; (V) greater than 0% to 0.5% by weight of p-xylylene diisocyanate; and (c') greater than 0% to 0.5% by weight of at least one selected from the group consisting of benzyl isocyanate, 4-methylbenzyl isocyanate, and 4-cyanobenzyl isocyanate, based on the total weight of the composition.

According to an embodiment, there is provided a polymerizable composition, which comprises an isocyanate composition and a thiol, wherein the isocyanate composition comprises (a') 99% to less than 100% by weight of m-xylylene diisocyanate; (b') greater than 0% to 0.5% by weight of p-xylylene diisocyanate; and (c') greater than 0% to 0.5% by weight of at least one selected from the group consisting of benzyl isocyanate, 4-methylbenzyl isocyanate, and 4-cyanobenzyl isocyanate, based on the total weight of the isocyanate composition.

According to an embodiment, there is provided an optical material, which comprises a polythiourethane prepared from an isocyanate composition and a thiol, wherein the isocyanate composition comprises (a') 99% to less than 100% by weight of m-xylylene diisocyanate; (b') greater than 0% to 0.5% by weight of p-xylylene diisocyanate; and (c') greater than 0% to 0.5% by weight of at least one selected from the group consisting of benzyl isocyanate, 4-methylbenzyl isocyanate, and 4-cyanobenzyl isocyanate, based on the total weight of the composition.

According to an embodiment, there is provided a process for producing an optical lens, which comprises preparing a first amine composition comprising m-xylylenediamine; reducing the content of at least one of p-xylylenediamine, benzylamine, 4-methylbenzylamine, and 4-cyanobenzylamine in the first amine composition to obtain a second amine composition; synthesizing an isocyanate from the second amine composition to prepare an isocyanate composition; and mixing the isocyanate composition with a thiol and thermally curing the mixture in a mold.

Advantageous Effects of Invention

According to the embodiments, a high-quality optical lens can be produced by controlling the composition of an isocyanate used in the production of a polythiourethane-based optical lens.

That is, it is possible to effectively satisfy the physical properties of a final optical lens by using an isocyanate composition comprising 99% by weight or more of m-XDI for high-quality optical lenses and having controlled amounts of specific kinds of isomers and monoisocyanates that may deteriorate the physical properties of the optical lens.

That is, a polythiourethane prepared from the isocyanate composition can satisfy not only such properties as refractive index, Abbe number, transparency, and the like, basically required for optical lenses, but also such characteristics as yellowness index, stria, cloudiness, glass transition temperature, mechanical properties, and the like. Therefore, it can be advantageously used in the field of eyeglass lenses, camera lenses, and the like.

DETAILED DESCRIPTION FOR CARRYING OUT THE INVENTION

Hereinafter, the present invention will be described in detail with reference to the examples. The examples are not limited to those described below. Rather, they may be modified into various forms as long as the gist of the invention is not altered.

In this specification, when a part is referred to as "comprising" an element, it is to be understood that the part may comprise other elements as well.

Further, all numbers and expression related to the quantities of components, reaction conditions, and the like used herein are to be understood as being modified by the term "about," unless otherwise indicated.

The terms first, second, and the like are used herein to describe various elements, and the elements should not be limited by the terms. The terms are used only for the purpose of distinguishing one element from another.

According to an embodiment, there is provided a process for preparing an isocyanate composition, which comprises preparing a first amine composition comprising m-xylylenediamine; reducing the content of at least one of p-xylylenediamine, benzylamine, 4-methylbenzylamine, and 4-cyanobenzylamine in the first amine composition to obtain a second amine composition; and synthesizing an isocyanate from the second amine composition.

Hereinafter, each step will be described in detail.

A first amine composition comprising m-xylylenediamine is prepared in the step of preparing the first amine composition.

The first amine composition may be prepared or by purchasing a commercially available one.

The first amine composition comprises m-xylylenediamine as a main component. However, the first amine composition may comprise isomers (e.g., p-xylylenediamine) and monoisocyanates (e.g., benzylamine, 4-methylbenzylamine, 4-cyanobenzylamine, and the like) in addition to m-xylylenediamine as the main component. These may be generated as byproducts during the synthesis of m-xylylenediamine as the main component.

Hereinafter, the procedures in which p-xylylenediamine, benzylamine, 4-methylbenzylamine, and 4-cyanobenzylamine are generated will be described while the process of preparing m-xylylenediamine is illustrated.

In order to prepare m-xylylenediamine, an aromatic mixture is first obtained by catalyst reforming of a naphtha raw material in a conventional BTX process, and m-xylene is then extracted from the aromatic mixture.

Subsequently, as shown in Reaction Scheme 1 below, isophthalonitrile is prepared from m-xylene (Step A), and m-xylylenediamine is prepared from isophthalonitrile (Step B).

[Reaction Scheme 1]

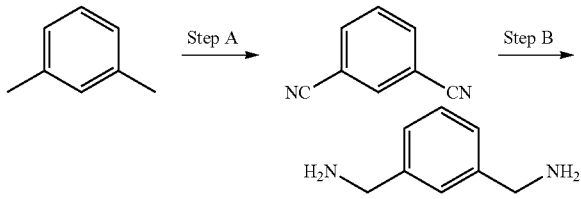

For example, the preparation of m-xylylenediamine from m-xylene may be carried out by a method that comprises the following steps, as illustrated in U.S. Pat. No. 8,212,080: (i) ammoxidizing m-xylene by a gas-phase catalytic reaction of ammonia and an oxygen-containing gas in the presence of a catalyst to produce an ammoxidized gas containing dicyanobenzene; (ii) subjecting the ammoxidized gas to direct contact with an organic solvent so that dicyanobenzene is absorbed in the organic solvent to thereby obtain a solution containing dicyanobenzene; (iii) distilling the solution containing dicyanobenzene to remove some or all of the compounds having lower boiling points than dicyanobenzene together with the organic solvent to thereby obtain molten dicyanobenzene; (iv) dissolving the molten dicyanobenzene in a liquid ammonia solvent or a mixed solvent of one or more aromatic hydrocarbons and liquid ammonia to obtain a solution; (v) removing some or all of the insoluble components in the solution to separate the liquid; and (vi) hydrogenating dicyanobenzene in a liquid phase as contained in the liquid in the presence of a catalyst.

The first amine composition obtained through the above synthesis routes further comprises isomers, monoisocyanates, and the like in addition to m-xylylenediamine.

As an example, the first amine composition may further comprise p-xylylenediamine. Specifically, a fraction of p-xylene may be contained in m-xylene extracted in the BTX process, and p-xylene may be converted to p-xylylenediamine through the above Steps A and B (see Reaction Scheme 2 below).

[Reaction Scheme 2]

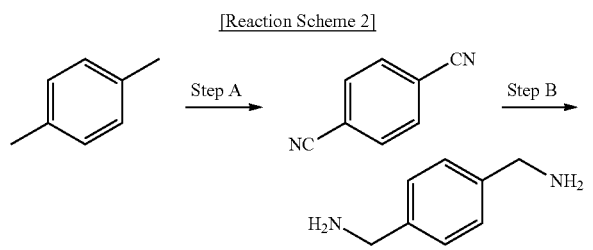

As another example, the first amine composition may further comprise benzylamine.

Specifically, a fraction of toluene may be contained in m-xylene extracted in the BTX process, and toluene may be converted to benzylamine through the above Steps A and B (see Reaction Scheme 3 below).

[Reaction Scheme 3]

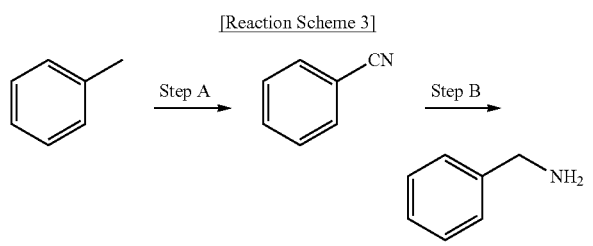

As another example, the first amine composition may further comprise 4-methylbenzylamine.

Specifically, a fraction of p-xylene may be contained in m-xylene extracted in the BTX process, and only one of the methyl groups in p-xylene participates in the reaction of the above Step A to produce 1-cyano-4-methylbenzene (or p-tolunitrile), which may be converted to 4-methylbenzylamine through the above Step B (see Scheme 4 below).

[Reaction Scheme 4]

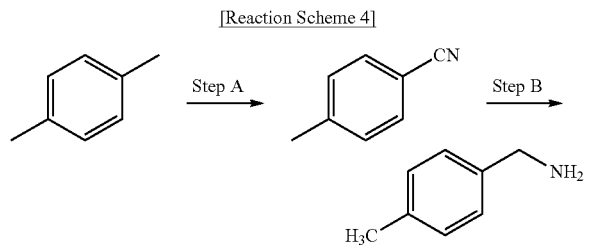

As another example, the first amine composition may further comprise 4-cyanobenzylamine.

Specifically, a fraction of p-xylene may be contained in m-xylene extracted in the BTX process, and p-xylene may be converted to p-dicyanobenzene (or terephthalonitrile) through the above Step A. Then, only one of the cyano groups in p-dicyanobenzene participates in the reaction of the above Step B to produce 4-cyanobenzylamine (see Scheme 5 below).

[Reaction Scheme 5]

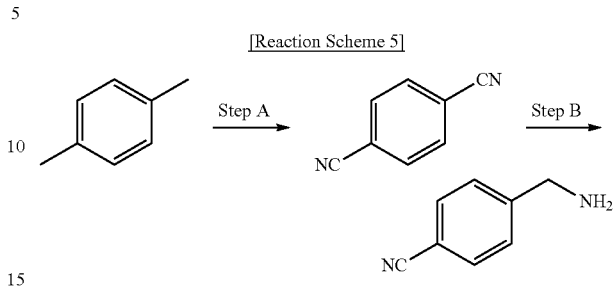

Accordingly, the first amine composition may comprise (a) m-xylylenediamine, (b) p-xylylenediamine, and (c) at least one selected from the group consisting of benzylamine, 4-methylbenzylamine, and 4-cyanobenzylamine.

The content of each of the components (a) to (c) contained in the first amine composition is not particularly limited.

As an example, the first amine composition may comprise (a) 90% to less than 100% by weight of m-xylylenediamine; (b) greater than 0% to 5% by weight of p-xylylenediamine; and (c) greater than 0% to 5% by weight of at least one selected from the group consisting of benzylamine, 4-methylbenzylamine, and 4-cyanobenzylamine.

As another example, the first amine composition may comprise (a) 90% to less than 99% by weight of m-xylylenediamine; (b) greater than 0.5 to 5% by weight of p-xylylenediamine; and (c) greater than 0.5 to 5% by weight of at least one selected from the group consisting of benzylamine, 4-methylbenzylamine, and 4-cyanobenzylamine.

When the contents of the components (b) and (c) in an amine composition are as described above, it does not cause any particular problems for use in a conventional application. However, if the amine composition is used in optical lens applications, the contents of the components (b) and (c) may have an impact on the optical characteristics of a product. Therefore, it is necessary to appropriately adjust the contents of the components (b) and (c) contained in the amine composition by the following procedures.

In the step of obtaining a second amine composition, the content of at least one of p-xylylene diamine, benzylamine, 4-methylbenzylamine, and 4-cyanobenzylamine in the first amine composition prepared above is reduced, to thereby obtain the second amine composition.

Preferably, the content of p-xylylenediamine and the content of at least one of benzylamine, 4-methylbenzylamine, and 4-cyanobenzylamine in the first amine composition are reduced to obtain the second amine composition whose composition is controlled.

More preferably, the contents of all of p-xylylenediamine, benzylamine, 4-methylbenzylamine, and 4-cyanobenzylamine in the first amine composition are reduced to obtain the second amine composition whose composition is controlled.

As an example, the content of each amine component in the first amine composition is controlled by taking advantage of the differences in the boiling points and the freezing points thereof to obtain the second amine composition. The boiling point and the freezing point of each amine component are summarized in Table 1 below.

TABLE 1

| Amine component | Formula | Boiling point (° C.) | Freezing point (° C.) |
|---|---|---|---|
| m-xylylenediamine | 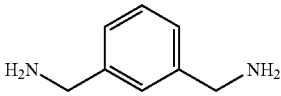 | 265 | 14 |
| p-xylylenediamine | 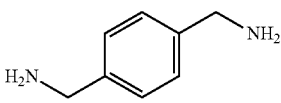 | 230 | 63 |
| benzylamine | 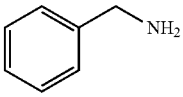 | 185 | 10 |
| 4-methylbenzylamine | 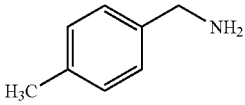 | 195 | 13 |
| 4-cyanobenzylamine | 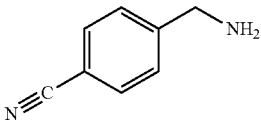 | 275 | 20 |

For example, the second amine composition may be prepared by controlling the contents of the amine components in the composition through such a method as distillation, recrystallization, and the like.

According to an example, the contents of p-xylylenediamine and 4-cyanobenzylamine may be controlled by removing the compounds precipitated through recrystallization based on the differences in the freezing point between them and m-xylylenediamine. The contents of benzylamine and 4-methylbenzylamine may be controlled by removing them through distillation based on the differences in the boiling point between them and m-xylylenediamine.

According to a specific example, the step of obtaining the second amine composition may be carried out by a method comprising at least one of removing the distilled compounds while the first amine composition is heated to 100 to 185° C. under a reduced pressure; and removing the precipitated compounds while the first amine composition is cooled to 15 to 18° C.

According to another specific example, the step of obtaining the second amine composition may be carried out by removing the distilled compounds while the first amine composition is heated to 100 to 185° C. under a reduced pressure; and then removing the precipitated compounds while the first amine composition is cooled to 15 to 18° C.

In such event, the compounds distilled during the heating may include benzylamine and 4-methylbenzylamine; and the compounds precipitated during the cooling may include p-xylylenediamine and 4-cyanobenzylamine.

Further, since the distillation is carried out under a reduced pressure, the compounds (benzylamine, 4-methylbenzylamine, and the like) can be removed even if the first amine composition is heated to a temperature (100 to 185° C.) lower than their boiling points. As a more specific example, the distillation may be performed by elevating the temperature to 100 to 180° C., 120 to 180° C., 140 to 180° C., 160 to 180° C., 120 to 160° C., or 140 to 160° C. under a reduced pressure.

The second amine composition whose composition is specifically controlled may be obtained through the above procedures.

For example, the second amine composition may comprise 99% to less than 100% by weight, specifically 99.5% to less than 100% by weight, more specifically 99.7% to less than 100% by weight of m-xylylenediamine (m-XDA).

Further, the second amine composition may comprise greater than 0% to 0.5% by weight, specifically greater than 0% to 0.3% by weight, more specifically greater than 0% to 0.15% by weight of p-xylylenediamine (p-XDA).

In addition, the second amine composition may comprise greater than 0% to 0.5% by weight, specifically greater than 0% to 0.3% by weight, more specifically greater than 0% to 0.15% by weight of at least one selected from the group consisting of benzylamine, 4-methylbenzylamine, and 4-cyanobenzylamine.

In such event, the second amine composition may comprise greater than 0% to 0.15% by weight, specifically greater than 0% to 0.1% by weight, more specifically greater than 0% to 0.05% by weight of each of benzylamine, 4-methylbenzylamine, and 4-cyanobenzylamine.

According to a preferred example, the second amine composition may comprise (a) 99% to less than 100% by weight of m-xylylenediamine; (b) greater than 0% to 0.5% by weight of p-xylylenediamine; and (c) greater than 0% to 0.5% by weight of at least one selected from the group consisting of benzylamine, 4-methylbenzylamine, and 4-cyanobenzylamine, based on the total weight of the composition.

According to another preferred example, the second amine composition may comprise (a) 99.7% to less than 100% by weight of m-xylylenediamine; (b) greater than 0% to 0.15% by weight of p-xylylenediamine; and (c) greater than 0% to 0.15% by weight of at least one selected from the group consisting of benzylamine, 4-methylbenzylamine, and 4-cyanobenzylamine, based on the total weight of the composition.

According to another preferred example, the second amine composition may comprise (a) 99.7% to less than 100% by weight of m-xylylenediamine; (b) greater than 0% to 0.15% by weight of p-xylylenediamine; and (c) greater than 0% to 0.05% by weight of each of benzylamine, 4-methylbenzylamine, and 4-cyanobenzylamine, based on the total weight of the composition.

In the step of preparing an isocyanate composition, an isocyanate is synthesized from the second amine composition to thereby produce the isocyanate composition.

An isocyanate may be synthesized from an amine by a phosgene method or a non-phosgene method.

According to an example of the phosgene method, as shown in Reaction Scheme 6 below, an amine may be reacted with hydrochloric acid at a temperature of 30° C. or lower in an ester-based solvent to obtain an amine hydrochloride, which may then be reacted with phosgene at 120 to 170° C., to thereby synthesize an isocyanate.

[Reaction Scheme 6]

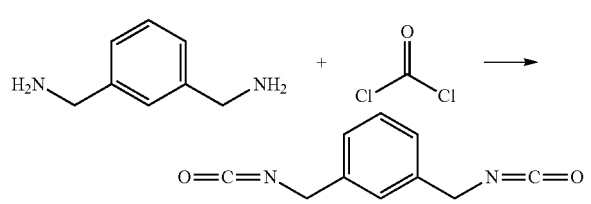

According to an example of the non-phosgene process, as shown in Reaction Scheme 7 below, an amine may be reacted with a halo $C_{1-10}$ alkyl chloroformate or a halo di-$C_{1-10}$ alkyl carbonate to prepare a biscarbamate, which may then be thermally decomposed in the presence of a catalyst at a high temperature of 130 to 250° C. in a solvent, to thereby synthesize an isocyanate.

[Reaction Scheme 7]

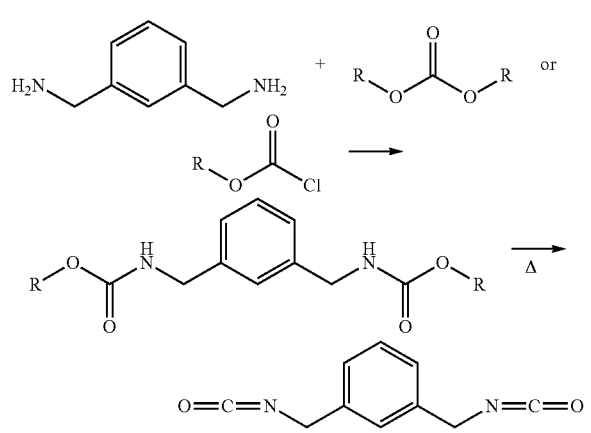

In the above Reaction Scheme 7, R is halo $C_{1-10}$ alkyl.
Here, the halo may be fluoro, chloro, bromo, or iodo.
Preferably, the synthesis step of preparing the isocyanate composition may be carried out by reacting the second amine composition with phosgene or a halo $C_{1-10}$ alkyl chloroformate.

As shown in the above Reaction Schemes 6 and 7, m-xylylenediamine in the composition is converted to m-xylylene diisocyanate through the above synthesis routes. In addition, as illustrated in the following Reaction Schemes 8 to 11, p-xylylenediamine in the composition is converted to p-xylylene diisocyanate, benzylamine is converted to benzyl isocyanate, 4-methylbenzylamine is converted to 4-methylbenzyl isocyanate, and 4-cyanobenzylamine is converted to 4-cyanobenzyl isocyanate.

[Reaction Scheme 8]

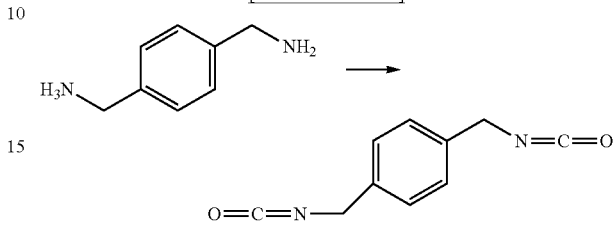

[Reaction Scheme 9]

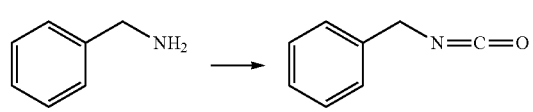

[Reaction Scheme 10]

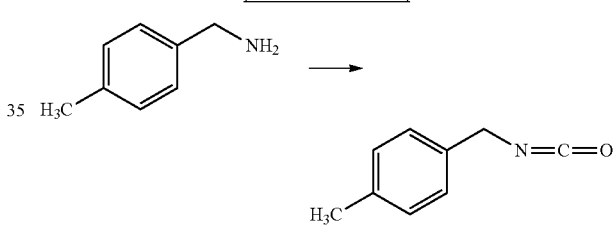

[Reaction Scheme 11]

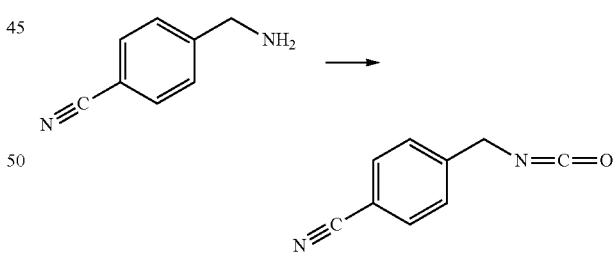

According to the embodiment, since an amine composition in which the content of m-xylylenediamine has been increased and the contents of p-xylylene diamine, benzylamine, 4-methylbenzylamine, and 4-cyanobenzylamine have been reduced is used, an isocyanate composition prepared therefrom may have an increased content of m-xylylene diisocyanate and reduced contents of p-xylylene diisocyanate, benzyl isocyanate, 4-methylbenzyl isocyanate, and 4-cyanobenzyl isocyanate.

According to an embodiment, there is provided an isocyanate composition prepared from a composition in which the types and contents of amines have been controlled.

That is, according to the embodiment, there is provided an isocyanate composition, which comprises (a') 99% to less than 100% by weight of m-xylene diisocyanate; (b') greater than 0% to 0.5% by weight of p-xylylene diisocyanate; and (c') greater than 0% to 0.5% by weight of at least one selected from the group consisting of benzyl isocyanate, 4-methylbenzyl isocyanate, and 4-cyanobenzyl isocyanate, based on the total weight of the composition.

The isocyanate composition according to the embodiment may comprise 99% to less than 100% by weight, specifically 99.5% to less than 100% by weight, more specifically 99.7% to less than 100% by weight of m-xylylene diisocyanate (m-XDI).

The isocyanate composition according to the embodiment may comprise greater than 0% to 0.5% by weight, specifically greater than 0% to 0.3% by weight, more specifically greater than 0% to 0.15% by weight, or greater than 0% to 0.1% by weight of p-xylylene diisocyanate (p-XDI).

The isocyanate composition according to the embodiment may comprise greater than 0% to 0.5% by weight, specifically greater than 0% to 0.3% by weight, more specifically greater than 0% to 0.2% by weight, or greater than 0% to 0.15% by weight of at least one selected from the group consisting of benzyl isocyanate, 4-methylbenzyl isocyanate, and 4-cyanobenzyl isocyanate.

In such event, the isocyanate composition according to the embodiment may comprise greater than 0% to 0.15% by weight, specifically greater than 0% to 0.1% by weight, more specifically greater than 0% to 0.05% by weight of each of benzyl isocyanate, 4-methylbenzyl isocyanate, and 4-cyanobenzyl isocyanate.

If m-xylylene diisocyanate is contained in the composition in an amount less than the above preferable range, not only the optical characteristics (especially, striae, transmittance, and the like) but also the mechanical properties (such as impact resistance, tensile strength, and the like) of the final product may be impaired due to nonuniformity in the polymerization reactivity of the composition and in the chemical structure of the cured product. Further, yellowing may occur depending on other components incorporated therein.

If p-xylylene diisocyanate is contained in the composition in an amount exceeding the above preferable range, the optical characteristics may be impaired as striae occur or the transmittance is lowered due to the nonuniform polymerization caused by differences in the reactivity or due to the crystallization caused by changes in the chemical structure of the polymer.

If benzyl isocyanate is contained in the composition in an amount exceeding the above preferable range, the equivalent ratios of the composition are changed due to decreases in the average number of functional groups in the composition, which affect the chemical structure of the polymer, resulting in deteriorations in the mechanical properties or the heat resistance such as glass transition temperature of the final product.

If 4-methylbenzyl isocyanate is contained in the composition in an amount exceeding the above preferable range, the equivalent ratios of the composition are changed due to decreases in the average number of functional groups in the composition, which affect the chemical structure of the polymer, resulting in deteriorations in the mechanical properties or the heat resistance such as glass transition temperature of the final product.

If 4-cyanolbenzyl isocyanate is contained in the composition in an amount exceeding the above preferable range, the equivalent ratios of the composition are changed due to decreases in the average number of functional groups in the composition, which affect the chemical structure of the polymer, resulting in deteriorations in the mechanical properties or the heat resistance such as glass transition temperature of the final product. Further, due to the influence of the cyano groups, yellowing may occur at the time of thermal curing for producing a lens or after the production of the lens depending on the external environment, thereby causing serious damage to the long-term reliability of the lens.

Therefore, a product produced from the isocyanate composition whose composition has been controlled as described above can satisfy excellent optical characteristics; and it can be advantageously used for the production of optical materials, specifically plastic optical lenses.

According to an embodiment, there is provided a polymerizable composition, which comprises the isocyanate composition as described above and a thiol.

That is, according to the embodiment, there is provided a polymerizable composition, which comprises an isocyanate composition and a thiol, wherein the isocyanate composition comprises (a') 99% to less than 100% by weight of m-xylylene diisocyanate; (b') greater than 0% to 0.5% by weight of p-xylylene diisocyanate; and (c') greater than 0% to 0.5% by weight of at least one selected from the group consisting of benzyl isocyanate, 4-methylbenzyl isocyanate, and 4-cyanobenzyl isocyanate, based on the total weight of the isocyanate composition.

The polymerizable composition may comprise the isocyanate composition and the thiol in a mixed state or in a separated state. That is, the isocyanate composition and the thiol in the polymerizable composition may be in a state of being compounded in contact with each other or separated from each other so as not to contact each other.

In the polymerizable composition, the molar ratio of SH group/NCO group in the composition may be 0.5 to 3.0, more specifically 0.8 to 1.3.

The thiol may be a thiol oligomer or a polythiol and may be used alone or as a mixture of two or more thereof.

Specific examples of the thiol include 3,3'-thiobis[2-[(2-mercaptoethyl)thio]-1-propanethiol, bis(2-(2-mercaptoethylthio)-3-mercaptopropyl)sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, bis(2-mercaptoethyl)sulfide, tetrakis(mercaptomethyl)methane, 2-(2-mercaptoethylthio)propane-1,3-dithiol, 2-(2,3-bis(2-mercaptoethylthio)propylthio)ethanethiol, bis(2,3-dimercaptopropanyl)sulfide, bis(2,3-dimercaptopropanyl)disulfide, 1,2-bis[(2-mercaptoethyl)thio]-3-mercaptopropane, 1,2-bis(2-(2-mercaptoethylthio)-3-mercaptopropylthio)ethane, 2-(2-mercaptoethylthio)-3-2-mercapto-3-[3-mercapto-2-(2-mercaptoethylthio)-propylthio]propylthio-propane-1-thiol, 2,2-bis-(3-mercaptopropionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propyl)thio)propyl)thio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11- dimercapto-3,6,9-trithiaundecane, pentaerythritol tetrakis(3-mercaptopropionate), trimethylolpropane tris(3-mercaptopropionate), pentaerythritol tetrakis(2-mercaptoacetate), bispentaerythritol ether hexakis(3-mercaptopropionate), 1,1,3,3-tetrakis(mercaptomethylthio) propane, 1,1,2,2-tetrakis(mercaptomethylthio)ethane, 4,6-bis(mercaptomethylthio)-1,3-dithiane, pentaerythritol tetrakis(2-mercaptoacetate), pentaerythritol tetrakis(3-mercaptopropionate), 2-(2,2-bis(mercaptodimethylthio)ethyl)-1,3-dithiane, and the like.

The polymerizable composition may further comprise such additives as an internal mold release agent, an ultraviolet absorber, a polymerization initiator, a heat stabilizer, a color correcting agent, a chain extender, a crosslinking agent, a light stabilizer, an antioxidant, a filler, and the like.

The internal release agent may include a fluorine-based nonionic surfactant having a perfluoroalkyl group, a hydroxyalkyl group, or a phosphate ester group; a silicone-based nonionic surfactant having a dimethylpolysiloxane group, a hydroxyalkyl group, or a phosphate ester group; an alkyl quaternary ammonium salt such as trimethylcetylammonium salt, trimethylstearyl salt, dimethylethylcetylammonium salt, triethyldodecylammonium salt, trioctylmethylammonium salt, and diethylcyclohexadodecylammonium salt; and an acidic phosphate ester. It may be used alone or in combination of two or more thereof.

As the ultraviolet absorber-based, benzophenone-based, benzotriazole-based, salicylate-based, cyanoacrylate-based, oxanilide-based, or the like may be used.

As the polymerization initiator, an amine-based, phosphorus-based, organosilicate-based, organic copper-based, organic gallium, organic zirconium, organic iron-based, organic zinc, organic aluminum, or the like may be used.

As the heat stabilizer, metal fatty acid salt-based, phosphorus-based, lead-based, organotin-based, or the like may be used alone or in combination of two or more thereof.

In addition, according to an embodiment, there is provided a polythiourethane prepared from the polymerizable composition as described above. That is, the polythiourethane may be prepared by polymerizing (and curing) the isocyanate composition and the thiol in the polymerizable composition.

Specific examples of the isocyanate compound are as described above.

The molar ratio of SH group/NCO group in the polymerization reaction may be 0.5 to 3.0, more specifically 0.8 to 1.3.

Further, in order to control the reaction rate during the polymerization reaction, a reaction catalyst, which is usually used in the production of polyurethane, may be added. As the curing catalyst (or polymerization initiator), a tin-based catalyst may be used. For example, dibutyl tin dichloride, dibutyl tin dilaurate, dimethyl tin dichloride, or the like may be used.

Since the polythiourethane is prepared from the isocyanate composition whose composition has been controlled as described above, its optical characteristics are excellent.

In addition, according to an embodiment, there is provided an optical material, which comprises the polythiourethane as described above.

That is, according to the embodiment, there is provided an optical material, which comprises a polythiourethane prepared from an isocyanate composition and a thiol, wherein the isocyanate composition comprises (a') 99% to less than 100% by weight of m-xylylene diisocyanate; (b') greater than 0% to 0.5% by weight of p-xylylene diisocyanate; and (c') greater than 0% to 0.5% by weight of at least one selected from the group consisting of benzyl isocyanate, 4-methylbenzyl isocyanate, and 4-cyanobenzyl isocyanate, based on the total weight of the composition.

The optical material may be produced by polymerizing (and curing) the isocyanate composition and the thiol in the polymerizable composition.

The optical material thus produced from the xylylene diisocyanate composition according to the embodiment has excellent optical properties. Therefore, the optical material can be advantageously used as a spectacle lens, a camera lens, or the like. The optical material may preferably be a polythiourethane-based lens, i.e., a plastic optical lens.

According to an embodiment, there is provided a process for producing an optical lens, which comprises preparing a first amine composition comprising m-xylylenediamine; reducing the content of at least one of p-xylylenediamine, benzylamine, 4-methylbenzylamine, and 4-cyanobenzylamine in the first amine composition to obtain a second amine composition; synthesizing an isocyanate from the second amine composition to prepare an isocyanate composition; and mixing the isocyanate composition with a thiol and thermally curing the mixture in a mold.

In the process for producing an optical lens, the step of preparing a first amine composition, the step of obtaining a second amine composition, and the step of preparing an isocyanate composition may be carried out according to the conditions and procedures as described in the process for producing an isocyanate composition. In the process for producing an optical lens, the isocyanate composition and the thiol are then mixed and thermally cured in a mold as in the step of thermal curing.

For this purpose, the isocyanate composition is first mixed with the thiol to prepare a polymerizable composition. The polymerizable composition is degassed under a reduced pressure and then injected into a mold for molding an optical material. Such degassing and mold injection may be performed, for example, at a temperature range of 20 to 40° C.

Once the composition is injected into the mold, polymerization is usually carried out by gradually heating the composition from a low temperature to a high temperature. The polymerization temperature may be, for example, 30 to 150° C., particularly 40 to 130° C. In addition, a reaction catalyst, which is conventionally used in the production of polythiourethane, may be employed in order to control the reaction rate. Specific examples of the reaction catalyst are as exemplified above.

The molded polythiourethane article prepared as a result is released from the mold to obtain a final optical lens. The optical lens thus produced is colorless and transparent and is excellent in such optical characteristics as refractive index and Abbe number.

The optical lens may have a refractive index in the range of 1.60 to 1.78, more specifically in the range of 1.65 to 1.75, even more specifically in the range of 1.69 to 1.75.

The optical lens may have an Abbe number of 20 or greater, and more specifically may be 30 or greater. For example, the optical lens may have an Abbe number in the range of 30 to 50, in the range of 31 to 50, in the range of 31 to 45, or in the range of 31 to 40.

The optical lens may have a light transmittance, for example, a light transmittance at a wavelength of 550 nm of 85.0% to 99.9%, more specifically 87.0% to 99.0% or 87.0% to 95.0%.

The optical lens may have a yellowness index (YI) of 25 or less, or 20 or less, and specifically may be in the range of 1 to 25, in the range of 1 to 20, in the range of 3 to 20, in the range of 5 to 15.

In addition, the optical lens may have a glass transition temperature (Tg) of 90° C. or greater or 95° C. or greater, specifically in the range of 95 to 130° C., in the range of 95 to 120° C., in the range of 98 to 120° C., in the range of 100 to 120° C., in the range of 95 to 115° C., or in the range of 98 to 115° C.

According to a preferred example, the optical lens may have a yellowness index (YI) of 1 to 20 and a light transmittance of 85 to 99% at a wavelength of 550 nm. Also, the optical lens may have an Abbe number of 30 to 45 and a glass transition temperature of 95 to 120° C.

Hereinafter, the present invention is explained in detail by Examples. The following Examples are intended to further illustrate the present invention, and the scope of the Examples is not limited thereto.

EXAMPLE

Comparative Examples 1 to 4: Preparation of Isocyanate Compositions

Amine-A, Amine-B, Amine-C, and Amine-D compositions having the compositions listed in Table 2 below were used as the amine raw materials for the synthesis of isocyanates without further treatment thereof.

First, 15 parts by weight of each amine was dissolved in 78 parts by weight of o-dichlorobenzene to prepare an amine solution. Thereafter, 44 parts by weight of phosgene was dissolved in 52 parts by weight of o-dichlorobenzene to prepare a solution, which was cooled to 10° C. with a brine condenser and then placed in a reaction vessel. The amine solution prepared above was slowly added thereto at a temperature of 50° C. or lower. At this time, the amount of the amine solution added was adjusted to 5 moles of phosgene per 1 mole of amine. Thereafter, the reaction vessel was sealed, and the reaction solution was stirred for 2 hours. After further reaction for 3 hours at a temperature of 140° C. and a pressure of 3 kg/cm$^2$, the hydrochloric acid gas produced during the reaction was discharged. Upon completion of the reaction, the excessive phosgene was removed by a distillation process. The product was purified by fractional distillation under a reduced pressure to produce an m-xylene diisocyanate composition.

Examples 1: Preparation of an Isocyanate Composition

Step (1): Preparation of an Amine Composition

An amine composition comprising 81.1% by weight of m-XDI, 4.5% by weight of p-XDI, 3.7% by weight of benzylamine, 5.6% by weight of 4-methylentenamine, and 5.1% by weight of 4-cyanobenzylamine was prepared.

Step (2): Controlling the Content of Each Component in the Amine Composition

The amine composition prepared above was fed to a five-stage distillation apparatus, and the distillation was carried out by increasing the temperature from room temperature to about 180° C. under a reduced pressure. During distillation, benzylamine and 4-methylbenzylamine were sequentially distilled off. Thereafter, p-xylylenediamine and 4-cyanobenzylamine were sequentially precipitated and removed while the temperature was lowered to 20° C.

The composition thus obtained was named "Amine-E" and analyzed by gas chromatography (GC). The composition is summarized in Table 2 below.

Step (3): Synthesis of an Isocyanate

An isocyanate was synthesized using the Amine-E composition in the same manner as in Comparative Examples 1 to 4 to thereby obtain an isocyanate composition.

TABLE 2

| Amine component (wt. %) | Amine-A | Amine-B | Amine-C | Amine-D | Amine-E |
|---|---|---|---|---|---|
| m-XDA | 93.25 | 95.21 | 93.22 | 93.22 | 99.89 |
| p-XDA | 4.63 | 0.12 | 0.13 | 0.31 | 0.08 |
| Benzylamine | 0.52 | 3.61 | 0.33 | 0.21 | <0.01 |
| 4-methyl-benzylamine | 0.39 | 0.21 | 5.55 | 0.71 | <0.01 |
| 4-cyano-benzylamine | 0.35 | 0.36 | 0.64 | 5.1 | <0.01 |
| Others | 0.86 | 0.49 | 0.13 | 0.45 | <0.03 |

The isocyanate compositions prepared in the above Comparative Examples and Examples were analyzed by gas chromatography (GC), and their compositions are summarized in Table 3 below.

TABLE 3

| Amine component (wt. %) | C. Ex. 1 | C. Ex. 2 | C. Ex. 3 | C. Ex. 4 | Ex. 1 |
|---|---|---|---|---|---|
| m-XDA | 93.2 | 95.21 | 93.4 | 93.3 | 99.88 |
| p-XDA | 4.7 | 0.15 | 0.15 | 0.28 | 0.09 |
| Benzyl isocyanate | 0.5 | 3.55 | 0.31 | 0.17 | <0.01 |
| 4-methylbenzy isocyanate | 0.39 | 0.26 | 5.7 | 0.73 | <0.01 |
| 4-cyanobenzyl isocyanate | 0.33 | 0.32 | 0.4 | 4.9 | <0.01 |
| Others | 0.88 | 0.51 | 0.04 | 0.62 | <0.03 |

Test Example: Evaluation of Optical Lenses 520 g of each isocyanate composition prepared in Example 1 and Comparative Examples 1 to 4, 479.3 g of 3,3'-thiobis[2-[(2-mercaptoethyl)thio]-1-propanethiol, 0.15 g of dibutyl tin dichloride as a curing catalyst, and 0.80 g of Zelec™ UN as an internal mold release agent were mixed uniformly to prepare a polymerizable composition.

The polymerizable composition was subjected to stirring in a nitrogen atmosphere at room temperature and a reduced pressure for 30 minutes to remove air bubbles, and it was filtered with a Teflon filter of 3 μm.

The filtered polymerizable composition was injected into a glass mold assembled with an adhesive tape using nitrogen pressure. The glass mold injected with the polymerizable composition was placed in a forced circulation oven, and the temperature was elevated from 25° C. to 120° C. at a rate of 5° C./min, followed by polymerization at 120° C. for 18 hours. Thereafter, the polymerized resin was further cured at 130° C. for 4 hours, and a lens was released from the glass mold to obtain each optical lens having a center thickness of about 1.2 mm.

The optical lenses produced from the isocyanate compositions of Example 1 and Comparative Examples 1 to 4 were evaluated for the physical properties as shown in Table 4 below.

(1) Refractive Index and Abbe Number

The optical lenses were measured for refractive index and Abbe number at 20° C. using an Abbe refractometer DR-M4 model manufactured by Atago Co.

(2) Yellowness Index and Optical Transmittance

The optical lenses were measured for chromaticity coordinates x and y using a spectrophotometer CM-5 manufactured by Minolta Co., from which their yellow indices were calculated with Equation 1 below. Further, the transmittance at a wavelength of 550 nm was measured from the spectrum obtained using the same instrument.

$$YI=(234x+106y+106)/y \quad \text{[Equation 1]}$$

(3) Glass Transition Temperature (Tg)

The optical lenses were measured for glass transition temperature (Tg) with a thermal mechanical analyzer (TMA Q400, TA Instruments Co.) by a penetration method (load of 50 g, pin line of 0.5 mm Φ, temperature elevation rate of 10° C./min).

(4) Stria 100 optical lenses were observed under a mercury lamp with naked eyes. The lenses having a nonuniform image were classified as having a stria, and the percentages thereof were calculated. As a result, if the percentage of the stria occurrence was 5% or less, it was evaluated as good, and if the percentage of the stria occurrence was 5% or more, it was evaluated as poor.

TABLE 4

|  | C. Ex. 1 | C. Ex. 2 | C. Ex. 3 | C. Ex. 4 | Ex. 1 |
| --- | --- | --- | --- | --- | --- |
| Refractive index (nd) | 1.6672 | 1.6674 | 1.6679 | 1.6673 | 1.6662 |
| Abbe number (ve) | 29.3 | 30.2 | 29.3 | 28.3 | 31.2 |
| optical transmittance (%) | 85 | 80 | 81 | 75 | 90 |
| Tg (° C.) | 95 | 85 | 73 | 80 | 103 |
| Yellowness index | 33 | 35 | 37 | 72 | 12 |
| Stria | Poor (15%) | Poor (18%) | Poor (9%) | Poor (11%) | Good (3%) |

As confirmed from Table 4 above, the optical lens produced from the isocyanate compositions of Example 1 whose composition was controlled to desirable ranges was excellent in all of the refractive index, Abbe number, transmittance, Tg, yellowness index, and stria.

In contrast, the lenses produced from the isocyanate compositions of Comparative Example 1 to 4 that fell outside the desirable ranges were poor in at least one of the tested characteristics.

In particular, the optical lens produced from the composition of Comparative Example 1 having an excessive amount of p-XDI was poor in terms of the light transmittance, Abbe number, and stria. The optical lens produced from the composition of Comparative Example 2 having an excessive amount of benzyl isocyanate was poor in terms of the light transmittance, glass transition temperature, yellowness, and stria. The optical lens produced from the composition of Comparative Example 3 having an excessive amount of 4-methylbenzyl isocyanate was poor in terms of the light transmittance, glass transition temperature, yellowness, and stria. The optical lens produced from the composition of Comparative Example 4 having an excessive amount of 4-cyanobenzyl isocyanate was poor in terms of the light transmittance, glass transition temperature, yellowness, and stria; and it especially had the most serious defect in yellowness.

The invention claimed is:

1. A process for preparing an isocyanate composition, which comprises:
   preparing a first amine composition comprising m-xylylenediamine;
   reducing the content of at least one of p-xylylenediamine, benzylamine, 4-methylbenzylamine, and 4-cyanobenzylamine in the first amine composition to obtain a second amine composition; and
   synthesizing an isocyanate from the second amine composition to produce the isocyanate composition,
   wherein the step of synthesizing the isocyanate is carried out by reacting the second amine composition with phosgene, a halo $C_{1-10}$ alkyl chloroformate, or a halo di-$C_{1-10}$ alkyl carbonate.

2. The process for preparing an isocyanate composition of claim 1, wherein the second amine composition comprises:
   (a) 99% to less than 100% by weight of m-xylylenediamine;
   (b) greater than 0% to 0.5% by weight of p-xylylenediamine; and
   (c) greater than 0% to 0.5% by weight of at least one selected from the group consisting of benzylamine, 4-methylbenzylamine, and 4-cyanobenzylamine, based on the total weight of the composition.

3. The process for preparing an isocyanate composition of claim 1, wherein the second amine composition comprises:
   (a) 99.7% to less than 100% by weight of m-xylylenediamine;
   (b) greater than 0% to 0.15% by weight of p-xylylenediamine; and
   (c) greater than 0% to 0.05% by weight of each of benzylamine, 4-methylbenzylamine, and 4-cyanobenzylamine, based on the total weight of the composition.

4. The process for preparing an isocyanate composition of claim 1, wherein the step of obtaining the second amine composition is carried out by reducing the contents of all of p-xylylene diamine, benzylamine, 4-methylbenzylamine, and 4-cyanobenzylamine in the first amine composition.

5. The process for preparing an isocyanate composition of claim 1, wherein the step of obtaining the second amine composition is carried out by a method comprising at least one of:
   removing the distilled compounds while the first amine composition is heated to 100 to 185° C. under a reduced pressure; and
   removing the precipitated compounds while the first amine composition is cooled to 15 to 18° C.

6. The process for preparing an isocyanate composition of claim 1, wherein the step of obtaining the second amine composition is carried out by removing the distilled compounds while the first amine composition is heated to 100 to 185° C. under a reduced pressure; and then removing the precipitated compounds while the first amine composition is cooled to 15 to 18° C.

7. The process for preparing an isocyanate composition of claim 1, wherein the isocyanate composition comprises:
   (a') 99% to less than 100% by weight of m-xylylene diisocyanate;
   (b') greater than 0% to 0.5% by weight of p-xylylene diisocyanate; and
   (c') greater than 0% to 0.5% by weight of at least one selected from the group consisting of benzyl isocyanate, 4-methylbenzyl isocyanate, and 4-cyanobenzyl isocyanate, based on the total weight of the composition.

8. A process for producing an optical lens, which comprises:
   preparing a first amine composition comprising m-xylylenediamine;
   reducing the content of at least one of p-xylylenediamine, benzylamine, 4-methylbenzylamine, and 4-cyanobenzylamine in the first amine composition to obtain a second amine composition;
   synthesizing an isocyanate from the second amine composition to prepare an isocyanate composition; and mixing the isocyanate composition with a thiol and thermally curing the mixture in a mold,
wherein the step of synthesizing the isocyanate is carried out by reacting the second amine composition with phosgene, a halo $C_{1-10}$ alkyl chloroformate, or a halo di-$C_{1-10}$ alkyl carbonate.

9. The process for producing an optical lens of claim 8, wherein the optical lens has a yellowness index (YI) of 1 to 20 and a light transmittance of 85 to 99% at a wavelength of 550 nm.

10. The process for producing an optical lens of claim 9, wherein the optical lens has an Abbe number of 30 to 45 and a glass transition temperature of 95 to 120° C.

* * * * *